United States Patent [19]

Ko et al.

[11] Patent Number: 5,271,522

[45] Date of Patent: Dec. 21, 1993

[54] INDIVIDUAL BANDAGE DISPENSER

[75] Inventors: Su-sen Ko, White Bear Township, Ramsey County; David C. Byram, River Falls, both of Minn.

[73] Assignee: Minnesota Mining and Manufacturing Company, St. Paul, Minn.

[21] Appl. No.: 46,101

[22] Filed: Jan. 22, 1993

Related U.S. Application Data

[63] Continuation of Ser. No. 418,643, Oct. 10, 1989, abandoned.

[51] Int. Cl.5 .............................................. B65H 1/08
[52] U.S. Cl. ...................................... 221/58; 221/46; 221/59
[58] Field of Search ........................... 221/33-35, 221/44, 46, 55, 56, 58, 59; 206/441

[56] References Cited

U.S. PATENT DOCUMENTS

| | | | |
|---|---|---|---|
| 1,490,070 | 12/1922 | Korth . | |
| 1,495,670 | 5/1924 | Burridge . | |
| 1,689,571 | 10/1928 | West . | |
| 1,692,156 | 11/1928 | Carruthers | 221/34 |
| 3,189,219 | 6/1965 | Holzworth et al. | 221/131 |
| 3,202,316 | 8/1965 | Silver | 221/59 |
| 3,343,716 | 9/1967 | Peebles | 221/46 |
| 3,459,329 | 8/1969 | Mochizuki et al. | 221/34 |
| 3,520,403 | 7/1970 | Moshel | 206/63.2 |
| 3,835,992 | 9/1974 | Adams | 206/441 X |
| 4,469,243 | 9/1984 | Ito et al. | 221/34 |
| 4,562,938 | 1/1986 | Loder | 221/46 |
| 4,585,145 | 4/1986 | Pitroda | 221/58 |
| 4,586,629 | 5/1986 | Loder | 221/46 |
| 4,586,630 | 5/1986 | Loder | 221/46 |
| 4,586,631 | 5/1986 | Loder | 221/58 |
| 4,614,183 | 9/1986 | McCracken | 1281/132 R |
| 4,648,530 | 3/1987 | Granger | 221/34 |
| 4,653,666 | 3/1987 | Mertens | 221/45 |
| 4,674,634 | 6/1987 | Wilson | 206/554 |
| 4,770,320 | 9/1988 | Miles et al. | 221/33 |
| 4,781,306 | 11/1988 | Smith | 221/33 |
| 5,143,250 | 9/1992 | Freitag | 221/59 |

FOREIGN PATENT DOCUMENTS 656328  8/1951  United Kingdom ................. 73/E3

Primary Examiner—Joseph E. Valenza
Attorney, Agent, or Firm—Gary L. Griswold; Walter N. Kirn; Dale A. Bjorkman

[57] ABSTRACT

A dispenser for bandages is provided wherein bandages adhered to successive bandages along opposite ends of the bandage are dispensed from a box between a pair of flexible fingers extending into an opening in the top wall of the box. Various configurations for the stack of bandages to be provided in the box are also disclosed.

5 Claims, 4 Drawing Sheets

INDIVIDUAL BANDAGE DISPENSER

This is a continuation of U.S. application Ser. No. 07/418,643 filed Oct. 10, 1989 now abandoned.

FIELD OF THE INVENTION

This invention relates to an improved dispenser of first aid bandages, and in one aspect, to a stack of first aid bandages joined in a stack to be readily dispensed.

BACKGROUND OF THE INVENTION

Individual self-adhering bandage strips are well known in the prior art, and are extremely useful for home treatment of minor cuts and abrasions. One such individual bandage product that has enjoyed a great deal of success in this area is the Bandaid Brand Sheer Strip. Individual self-adhering bandages are available in a number of sizes, with a popular size being ¾ inch × 3 inches.

Individual self-adhering bandages are typically sold in individually wrapped units that are provided in boxes of twenty to thirty bandages. These bandages are difficult to dispense and apply due to the packaging arrangements in which they are sold. For example, the individually wrapped bandages are difficult to take out of the box one at a time because they are sufficiently thin that it is hard to grasp one at a time. At times a folded end of one package will catch on another package, further hindering separation of the bandages. Once a bandage has been separated from the rest of the bandages in the box, the wrapper must be removed in order to apply the bandage to the skin. The wrappers are usually designed to be torn apart by pulling on tabs at one end of the package, or by pulling on a little red string that will in turn tear the side of the package. Thus, removing the wrapper from each individual bandage may require a fair amount of finger dexterity. This process is also complicated when the injury to be protected by the bandage is on one of the hands.

U.S. Pat. No. 4,674,634 to Wilson discloses a package for dispensing reclosable plastic bags. The bags are arranged in a stack and are adhered one to another along alternately opposite edges of the bags. These bags are placed in a box having an opening in the upper surface of the box with the top bag in the stack extending through the opening. The user withdraws the bag through the opening in the top of the box, and the adhesive will pull the bottom edge of the next successive bag through the opening. The bags may be separated by peeling the adhesive coated edge of the bag dispensed from the next successive bag.

U.S. Pat. No. 4,653,666 to Mertens discloses a package for individually dispensing notepapers having a repositionable pressure-sensitive adhesive applied along one of the sheets. These notepapers are adhered one to another along opposite edges of successive sheets, and are dispensed from a card stock box with an opening in the top wall and having polymeric flaps extending into the opening that form an arcuate bend when a notepaper is withdrawn, thus reducing curl of the notepaper.

SUMMARY OF THE INVENTION

The present invention relates to an improved method of dispensing individual self-adhering bandages.

A dispenser package is provided for dispensing bandages from a box wherein the bandages are arranged in a stack with the bandages being releasably adhered to each other in the stack along opposite ends of successive bandages. The box has a bottom, side walls and a top wall, with the top wall having a rectangular opening extending generally centrally thereof and defined by opposed parallel margins. A pair of fingers are provided in the top wall so that one finger extends from one margin of the opening and the other finger extends from the opposite margin of the opening. The fingers terminate at terminal edges in an opposed spaced relation and each finger has free side edges movable in relationship to the side walls of the box. The fingers are positioned to normally rest on the top of the stack of bandages, and have the flexibility to form an arcuate bend transversely of the finger between the margin of the opening and the terminal edge of the finger during dispensing of bandages from the stack and having the resiliency to recover to rest on the top of the stack. Biasing means for urging the stack of bandages toward the opening is provided.

The dispenser is provided with the uppermost bandage in the stack extending through the opening in the top wall. As the user pulls on the free end of the uppermost bandage in the stack and withdraws it from the dispenser, the next successive bandage is pulled through the opening because it is adhesively attached to the distal end of the first bandage. Preferably, the width of the gap between the fingers on the top wall is between about 2 and 6 thicknesses of the thickest portion of the bandage. Most preferably, the gap is between about 2.5 and 4.5 thicknesses of the bandage. The first bandage does not separate from the second because the stress at the adhesive juncture of the bandages is applied in the shear direction. Once the first bandage is totally removed from the dispenser and the second bandage is partially drawn through the opening, the backing of the second bandage contacts a finger, imparting a force in the peel direction on the adhesive between the first and second bandage. The first bandage easily separates from the second bandage, leaving the second bandage in the dispensing position with the free end extending from the dispenser available for grasping by the user.

BRIEF DESCRIPTION OF THE DRAWING

The present invention will be further described with reference to the accompanying drawing wherein.

PREFERRED EMBODIMENTS OF THE INVENTION

Figure 1:
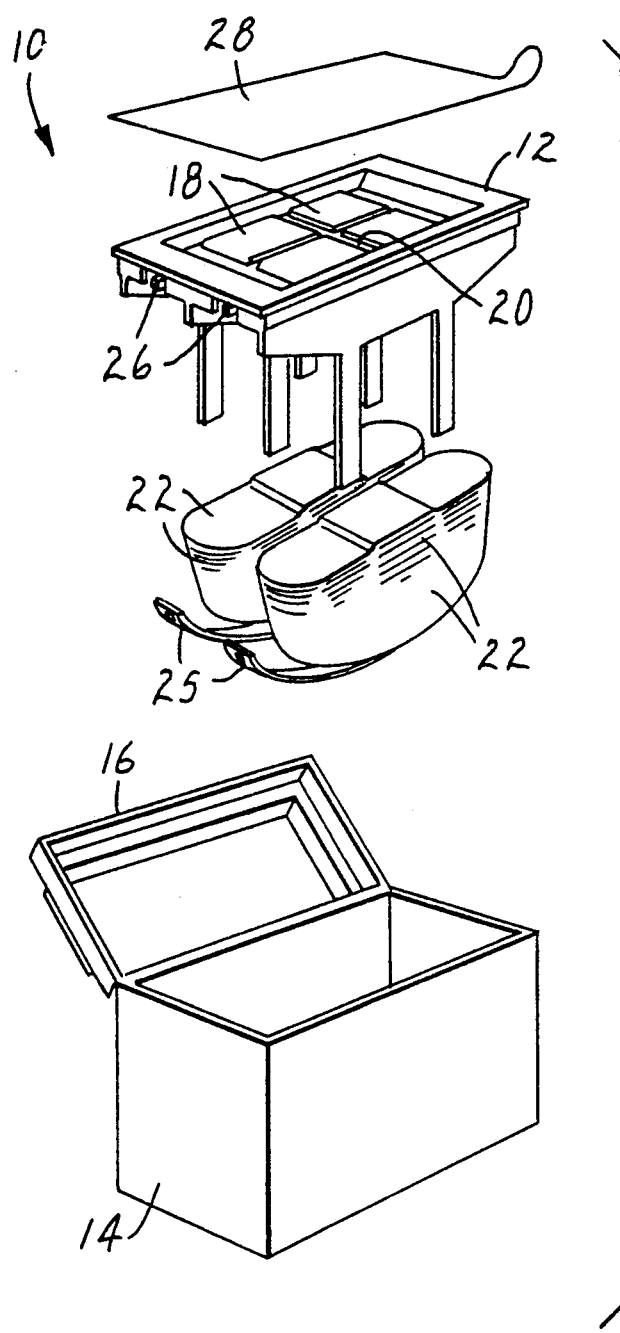
FIG. 1 is an exploded view of the individual bandage dispenser of the present invention.

Turning now to the drawing, FIG. 1 shows an exploded view of the individual bandage dispenser of the present invention 10. Top wall 12 for dispensing individual bandages as shown is slidably received in box 14. Top wall 12 is preferably anchored in place with respect to box 14 by fastening means. Box 14 is optionally provided with cover 16, which may be attached to box 14 with a mechanical hinge or a living hinge. Fingers 18 are provided on top wall 12, with gap 20 having a predetermined width between fingers 18. Bandages 22 are provided in a stacked formation with each individual bandage adhered to the successive bandage in the stack on alternating ends. Box 14 and fingers 18 are preferably prepared from a plastic material such as styrene or acrylonitrile/butadiene/styrene, or from a polypropylene such as high density polypropylene. Elastomeric tensioning device 25 is attached to top wall 12 at attachment points 26, thereby urging bandages 22 toward top wall 12. Tensioning device 25 is preferably prepared from an elastomeric material such as is used to prepare rubber bands. Examples of suitable materials include natural and synthetic rubbers, and especially Kraton rubber. Tensioning device 25 is but one biasing means that may be selected to urge bandages 22 toward top wall 12. Alternative biasing means include spring-like members made from wire or plastic or a polymeric foam that will exert an upward force on the stack of bandages. Tensioning device 25 is preferred because it provides uniform pressure to the stack of bandages 22 and naturally conforms to the bowed shape of the stack that results from having a centrally located absorbent pad on the bandage. Seal 28 may optionally be provided on top of top wall 12 in order to provide a sterile package unit to the consumer. The user gains access to the bandages by opening cover 16 and peeling off seal 28, which is then discarded.

Figure 2:
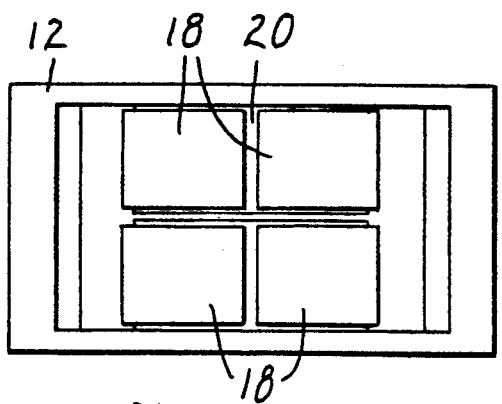
FIG. 2 is a top view of a bandage dispenser according to the present invention.

FIG. 2 is a top view of top wall 12, having two sets of fingers 18 arranged in a parallel array. Fingers 18 are arranged in opposing pairs with predetermined gap 20 between fingers 18. More than one set of fingers may be provided in order to increase the number of bandages that may be effectively dispensed from a single box. Alternatively, multiple sets of fingers make it possible to dispense bandages of different sizes. Fingers 18 may be integrally formed with top wall 12, as would result from a one-piece molding process, or may be separately adhered to top wall 12 with a pressure-sensitive adhesive, a hot melt adhesive, or the like. Fingers 18 may vary in size and shape, depending on the flexibility and friction properties desired. For example, fingers 18 may be of any width, but preferably are as wide as the bandage to be dispensed. Fingers 18 additionally may be straight or tapered, either in width or thickness. Fingers 18 may also have a smooth texture imparted to their surfaces, or may have a rough texture to moderate the amount of friction observed between the bandages and the underside of fingers 18.

Figure 3:
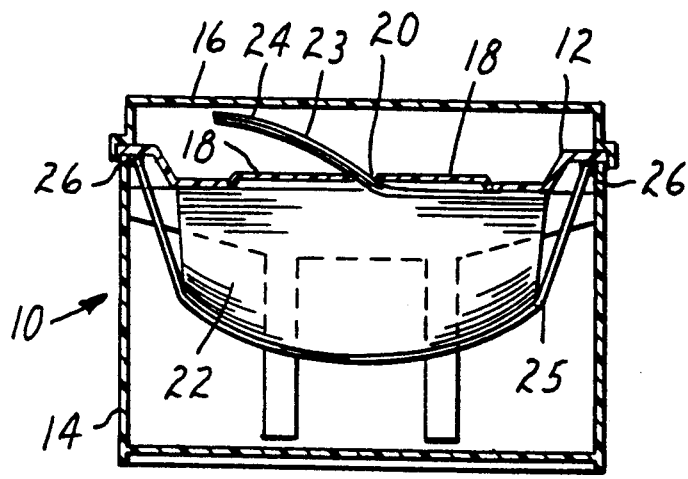
FIG. 3 is a side view, partly in section, of a dispenser.

FIG. 3 is a side view, partly in section, of dispenser 10. First bandage 23 having free end 24 extends through gap 20 and is available for grasping by the user. Preferably, attachment points 26 for tensioning device 25 are, as shown, above the level of top wall 12. In this configuration, tension is provided for even the last bandage in the stack as it progresses up through top wall 12.

Four factors together should be arranged such that the force required to withdraw a bandage from the dispenser is less than the shear strength of the adhesive interface between bandages, but greater than the peel strength of the adhesive interface between bandages. These four factors are (a) gap between the fingers, (b) finger flexibility, (c) force being applied by the biasing means, and (d) friction between the bandages and the underside of the fingers. All four factors act in harmony, and adjustments in one factor will modify the action of the others.

For illustrative purposes, modification of each of these four factors will be discussed in terms of how it will affect selection of appropriate gap width. It will be understood that such an analysis may now be conducted with respect to each of the identified factors.

When the fingers are very flexible, their ability to hold the next successive bandage in place in the dispenser is limited and the likelihood of multiple bandages being dispensed increases. To compensate for very flexible fingers, the gap between the fingers should be reduced. Similarly, when the amount of force being applied by the tensioning device in urging the bandages upward toward the fingers is low, the likelihood of multiple bandages being dispensed increases. To compensate for a low amount of force being provided by the tensioning device, the gap between the fingers should be reduced. Finally, when there is a low amount of friction between the bandages and the underside of the fingers, bandages will tend to slip out of the dispenser easily with the possibility of multiple dispensing of bandages. The texture of the underside of the fingers should be selected to match the particular material selected for use as the backing of the bandage. For example, a foam-type bandage backing will tend to stick to an extremely smooth surface, particularly when these surfaces contact over a period of time. To reduce the likelihood of sticking in this case, the underside of the fingers may be imparted with a series of ribs running in the travel direction of the bandage. In order to avoid sticking, but increase friction in removal of the bandage, the ribs may be provided perpendicular to the direction of travel of the bandage. When the bandage backing is made from a material that does not exhibit flow characteristics, a smooth texture on the underside of the fingers will result in very low friction interaction. In this case, higher friction may be provided by imparting a rough texture to the underside of the fingers, either as a random pattern or in a series of grooves, ribs or shapes such as a diamond pattern. In the alternative, the backing of the bandage may be surface treated or coated to enhance the slipperiness or stickiness of the backing. With respect to selection of proper gap width, a low-friction interaction between the bandages and the underside of the fingers may be compensated by reducing the distance of the gap between the fingers.

Typically, an appropriate selection of gap width will be from about 2 to 6 thicknesses of bandage. Preferably, the gap width will be from about 2.5 to 4.5 thicknesses of bandage.

Figure 4:
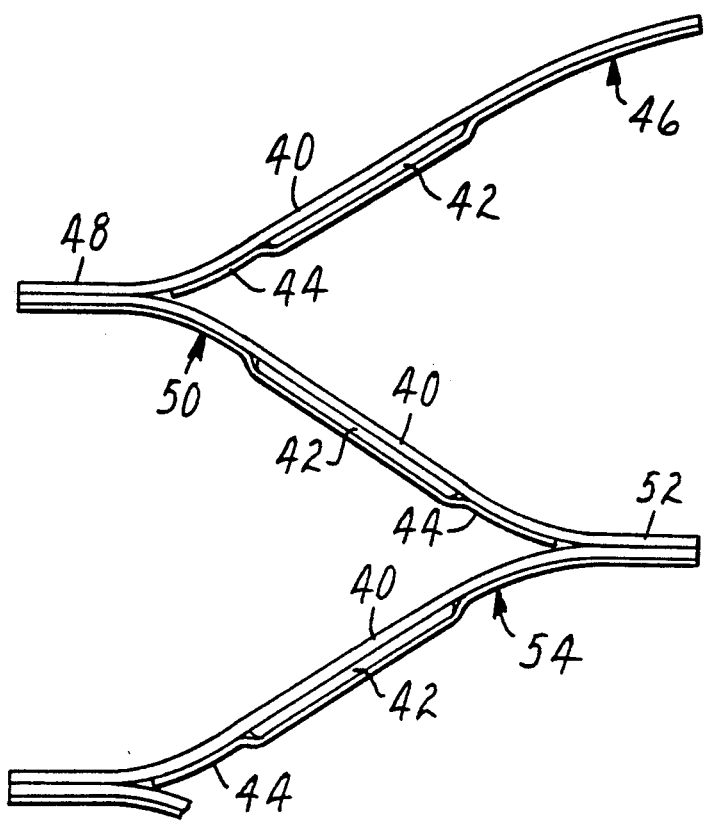
FIGS. 4 and 5 show a side view of a stack of bandages stacked in an alternating array according to the present invention.
Figure 5:
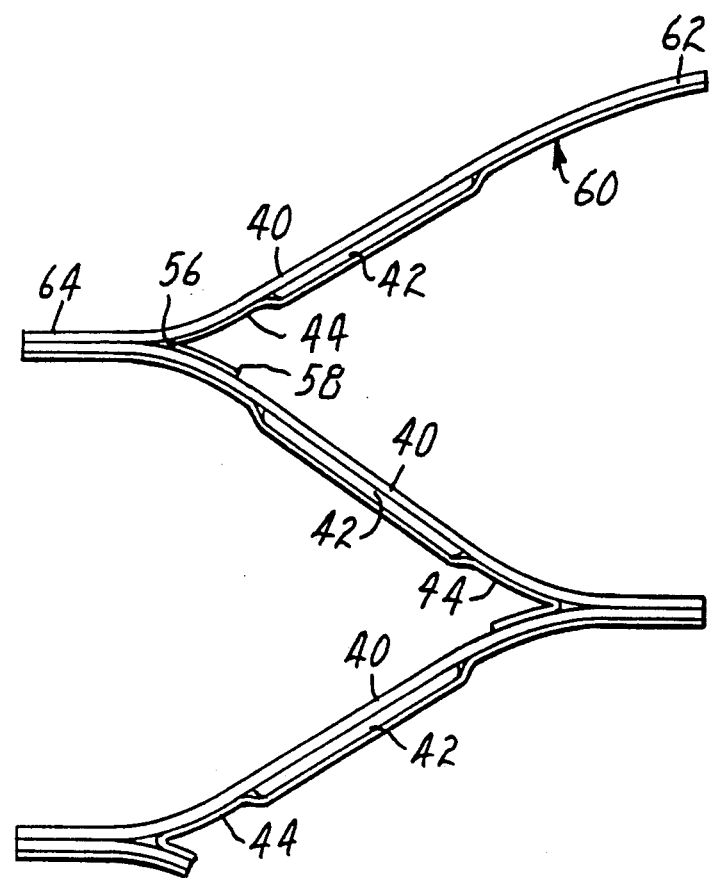

The various possible arrays of bandages are shown in FIGS. 4–7. The typical individual bandage comprises adhesive coated backing 40 with absorbent pad 42 centrally located thereon, and with liner 44 covering the adhesive coated side of backing 40. As shown in FIG. 4 the liner 44 of first bandage 46 is shortened so that distal end 48 of first bandage 46 extends beyond liner 44 and releasably adheres to the backing of second bandage 50. Similarly, liner 44 of second bandage 50 is short, so that the distal end 52 of second bandage 50 is releasably adhered to third bandage 54, and so on. FIG. 5 shows a similar array of bandages, except that instead of liner 44 being short, liner 44 is folded back at fold 56 to form tab 58. In the removal of first bandage 60, the user grasps free end 62 and removes bandage 60 from the dispenser 10. The thus removed bandage 60 has exposed adhesive at end 64 which may be located on the skin of the user. The user then grasps tab 58 and peels off liner 44 from bandage 60, simultaneously applying bandage 60 to the wound. This embodiment is particularly advantageous because only one hand is required to manipulate the bandage once removed from the box. If the box is additionally anchored in place, complete application of a bandage may be accomplished using only one hand.

Figure 6:
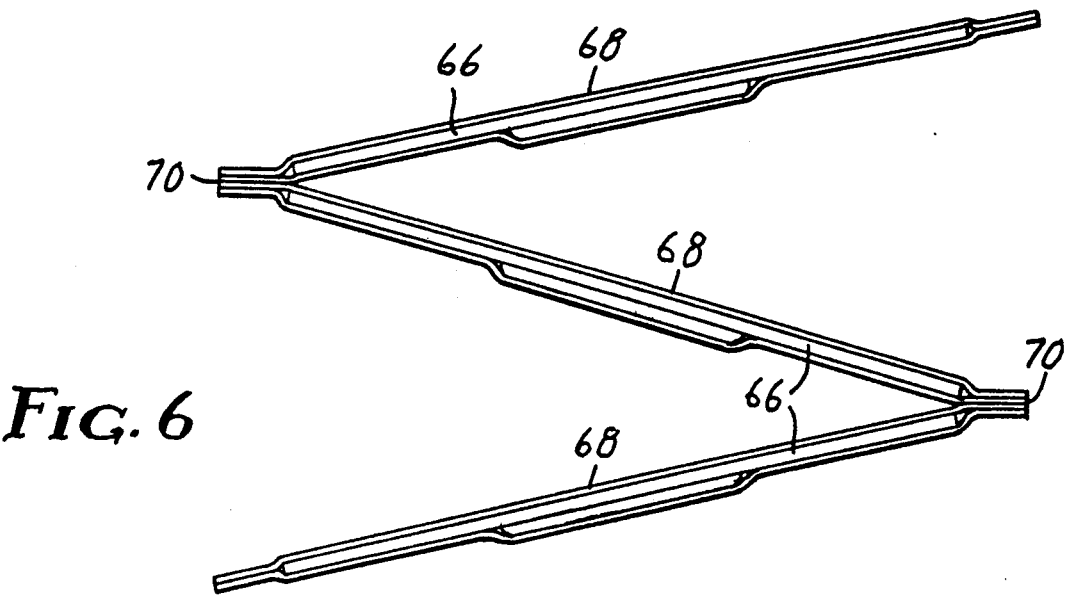
FIGS. 6 and 7 show a section view of a stack of bandages stacked in an alternating array according to the present invention.

FIG. 6 shows a section view of an alternative bandage configuration with bandages 66 completely enveloped in wrapper 68. Wrapper 68 of each bandage is adhered to the wrapper of the successive bandage along alternating ends with adhesive 70. This configuration allows bandages 66 to be provided as individually sterilized units.

Figure 7:
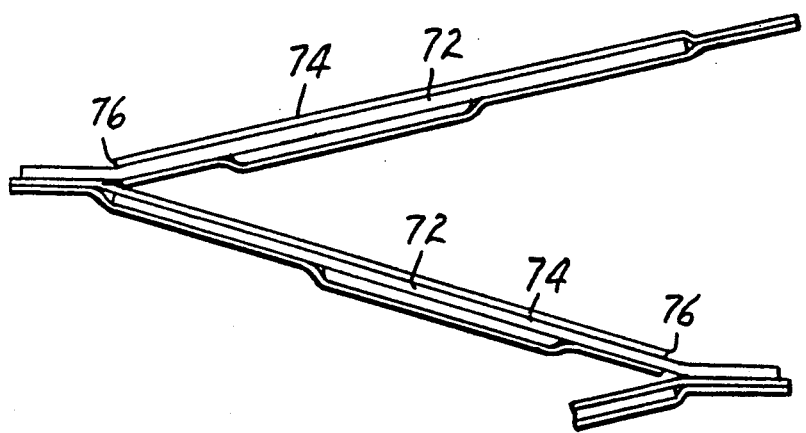

FIG. 7 shows a section view of an alternative wrapper configuration, wherein wrapper 74 acts as a release liner for bandage 72. No separate release liner is provided. Wrapper 74 envelopes bandage 72 and terminates at point 76 allowing the adhesive of bandage 72 to adhere to the wrapper of the next successive bandage.

Having thus described the present invention with respect to several embodiments, it is to be understood that other changes may be made without departing from the spirit and scope of the invention as defined by the appended claims.

I claim:

1. A dispenser package for dispensing bandages, said package comprising:
   bandages disposed in a stack, said bandages comprising a backing coated on one side with a pressure-sensitive adhesive and also comprising an absorbent pad centrally located on said pressure-sensitive adhesive coated side of the backing wherein said bandages are partially wrapped in a bandage wrapper and having one end of said bandage exposed, said bandages being releasably adhered to each other in the stack along opposite ends of successive bandages by the pressure-sensitive adhesive of one bandage adhering to the wrapper of the successive bandages;
   a box having a bottom, side walls and a top wall, said top wall having a rectangular opening extending generally centrally thereof and defined by opposed parallel margins;
   a pair of fingers, said fingers being disposed for one finger to extend from one margin of said opening and the other finger to extend from the opposite margin of said opening, said fingers terminating at terminal edges in opposed spaced related and each finger having free side edges movable in relationship to the side walls of the box, said fingers being positioned to normally rest on the top of said stack and said fingers having the flexibility to form an arcuate bend transversely of the finger between the margin of the opening and the terminal edge of the finger during dispensing of bandages from said stack and having the resiliency to recover to rest on the top of the stack, and
   biasing means for urging the stack of bandages toward the opening.

2. A dispenser package for dispensing bandages, said package comprising:
   bandages disposed in a stack, wherein said bandages comprise a backing coated on one side with a pressure-sensitive adhesive and also comprising an absorbent pad centrally located on said pressure-sensitive adhesive coated side of the backing,
   wherein said pressure-sensitive adhesive coated surface of said backing and said absorbent pad is partly covered by a liner and having one end of said pressure-sensitive adhesive coated surface of said backing exposed, said bandages being releasably adhered to each other in the stack along opposite ends of said bandages by the pressure-sensitive adhesives of one bandage adhering to an end portion of the backing of the successive backing;
   a box having a bottom, side walls and a top wall, said top wall having a rectangular opening extending generally centrally thereof and defined by opposed parallel margins;
   a pair of fingers, said fingers being disposed for one finger to extend from one margin of said opening and the other finger to extend from the opposite margin of said opening, said fingers terminating at terminal edges in opposed spaced relation and each finger having free side edges movably in relationship to the side walls of the box, said fingers being positioned to normally rest on the top of said stack and said fingers having the flexibility to form an arcuate bend transversely of the finger between the margin of the opening and the terminal edge of the finger during dispensing of bandages from said stack and having the resiliency to recover to rest on the top of the stack, and
   biasing means for urging the stack of bandages toward the opening.

3. A dispenser of claim 2 wherein said liner is folded back onto itself at the end of the bandage having the pressure-sensitive adhesive coated surface of the backing exposed, thereby providing a tab to assist in removing said liner from said bandage after positioning of the exposed pressure-sensitive adhesive surface on the skin.

4. A stack of bandages wherein each of said bandages comprise a backing coated on one side with a pressure-sensitive adhesive and an absorbent pad centrally located on said pressure-sensitive adhesive coated side of the backing,
   said pressure-sensitive adhesive coated surface of said backing and said absorbent pad being partly covered by a liner and having one end of said pressure-sensitive adhesive coated surface of said backing exposed, said bandages being releasably adhered to each other in the stack along opposite ends of said bandages by the pressure-sensitive adhesive of one bandage adhering to an end portion of the backing of the successive backing.

5. A stack of bandages according to claim 4 wherein said liner is folded back onto itself at the end of the bandage having the pressure-sensitive adhesive coated surface of the backing exposed, thereby providing a tab to assist in removing said liner from said bandage after positioning of the exposed pressure-sensitive adhesive surface on the skin.

* * * * *

UNITED STATES PATENT AND TRADEMARK OFFICE
CERTIFICATE OF CORRECTION

PATENT NO. : 5,271,522
DATED : Dec. 21, 1993
INVENTOR(S) : Su-Sen Ko and David C. Byram It is certified that error appears in the above-indentified patent and that said Letters Patent is hereby corrected as shown below:

On Cover Page item [75] line 2, delete "Ramsey County" and insert --Minn.--;

On Cover Page item [75] line 3, delete "both of Minn." and insert --Wisc.--

On column 6, line 40, delete "comprise" and insert --comprises--.

Signed and Sealed this

Sixteenth Day of January, 1996

Attest:

BRUCE LEHMAN

Attesting Officer    Commissioner of Patents and Trademarks